United States Patent [19]

Chidlow et al.

[11] 4,141,970
[45] Feb. 27, 1979

[54] METHOD FOR ENHANCING THE RESISTANCE OF NEW BORN MAMMALIAN YOUNG TO GASTRO-INTESTINAL INFECTIONS

[75] Inventors: John W. Chidlow; Philip Porter, both of Bedford, England

[73] Assignee: Internationale Octrooimaatschappij "Octropa" B.V., Rotterdam, Netherlands

[21] Appl. No.: 861,303

[22] Filed: Dec. 16, 1977

Related U.S. Application Data

[63] Continuation of Ser. No. 785,550, Apr. 7, 1977, abandoned, which is a continuation of Ser. No. 684,368, May 7, 1976, abandoned.

[30] Foreign Application Priority Data

May 7, 1975 [GB] United Kingdom ............... 19161/75

[51] Int. Cl.² ............................................ A61K 39/02
[52] U.S. Cl. ..................................................... 424/92
[58] Field of Search .......................................... 424/92

[56] References Cited

U.S. PATENT DOCUMENTS

| | | | |
|---|---|---|---|
| 3,127,318 | 3/1964 | Eversole et al. | 424/92 |
| 3,907,987 | 9/1975 | Wilson | 424/92 |

*Primary Examiner*—Sam Rosen
*Attorney, Agent, or Firm*—Barry Kramer

[57] ABSTRACT

The risk that the health of pregnant animals and their young will be impaired by gastro-intestinal infection is reduced by oral administration of endotoxins of the relevant pathogenic organisms to the pregnant animals. Combination of oral and parenteral administration is particularly beneficial, whether the animal is pregnant or not, in boosting immunological capacity. This technique is especially beneficial for mammals whose young acquire their passive immunity via the colostrum and hence through the gastro-intestinal wall, such as pigs, cows and sheep.

8 Claims, No Drawings

METHOD FOR ENHANCING THE RESISTANCE OF NEW BORN MAMMALIAN YOUNG TO GASTRO-INTESTINAL INFECTIONS

CROSS-REFERENCE TO RELATED APPLICATIONS

This application is a continuation of application Ser. No. 785,550 filed on Apr. 7, 1977, which, in turn, is a continuation of application Ser. No. 684,368 filed on May 7, 1976. Both of said latter applications are now abandoned.

This invention relates to improving the health of animals and is concerned with providing for the animal a regime which improves its health.

BACKGROUND OF THE INVENTION

Mortality immediately after parturition and amongst the newborn is high: thus, about 20% of pigs do not survive the first week of life, and about half of that number die because of gastro-intestinal disorders largely due to infection with pathogenic strains of one or more bacteria. Also gastro-intestinal disorders place a heavy strain on those that survive and contribute to poor growth and to poor weight-gain.

Such resistance as the newborn have to the bacterial infection which they are exposed to at birth or immediately after is acquired from the mothers. This protection (known as passive immune protection, because the antibodies conferring protection are received by the young animal, not generated by it) is, in modern stock-raising practice, put to severe test. Thus, with pigs, it is usual to bring sows into a common farrowing house a few days before parturition. Because of the change of environment and the trauma of parturition, natural resistance of the sows (especially those having their first litter) to infection is much diminished. In consequence, the pathogenic strains of bacteria such as E.coli that are already present (but in small population) in the gut multiply. When these pathogens are excreted, the newborn young are exposed to infection by them, even before they take their first suck. Fresh arrivals of sows about to farrow, and the piglets they duly bear, are exposed to increasing possibility of infection from pathogens excreted by the dams and litters already in the farrowing house.

Prior Art

We have previously described (see for example British Pat. No. 1,336,015) the oral administration of endotoxins to domestic animals to improve their resistance to gastro-intestinal infection, especially to young at the weaning stage.

It is known that, by giving parenteral injections of appropriate antigenic material (essentially bacterial endotoxins) before parturition, there is produced in the mother's blood an increased level of antibodies against the appropriate pathogen. These antibodies are transferred to the young for example either by transfer across the placenta or by transfer to the colostrum and thence by absorption through the gastro-intestinal wall of the suckling young into its bloodstream. The pig is an example of an animal whose young acquire passive immunity almost entirely via the colostrum and gastro-intestinal wall. Although without the passive immunity that is acquired the situation would be much worse, it is frequently found that the passive immunity is inadequate to cope with the highly infective environment described earlier.

The Invention(s)

We have now found that the risk that the health of pregnant animals and of their young will be impaired can be reduced by introducing into the intestine of the pregnant animal by way of the mouth endotoxins of a pathogenic bacterium causing a gastro-intestinal disorder.

The invention therefore provides a method of treating a pregnant animal to improve its health and that of its litter in which endotoxins of a pathogenic bacterium causing a gastro-intestinal disorder are introduced into the intestine of the animal by way of the mouth.

We have further found that the effective antibody activity generated in an animal by parenteral administration of endotoxis of pathogenic bacteria can be markedly improved by the oral adminstration of the endotoxins as described above to the animal, whether pregnant or not. When the animal is pregnant, (This is a preferred form of this related invention.) there is consequent benefit both to the mother and to her young.

Particularly for mammals whose young acquire at least part of their passive immunity via the colostrum and gastro-intestinal wall the further effect has been found that enhanced passive immunity is acquired by the young. The effort is especially important for those mammals, such as pigs, cows and sheep, where substantially all of the passive immunity of the young is acquired via the colostrum and gastro-intestinal wall.

Thus according to a particularly important aspect of the present invention, endotoxins of a pathogenic bacterium against which protection is desired are repeatedly administered orally (i.e. are introduced into the intestine by way of the mouth) to a pregnant animal whose young acquire at least part of their passive immunity via the colostrum and, towards the end of the gestation period, the endotoxins are also administered to the animal parenterally.

DETAIL OF THE INVENTION

Oral administration of endotoxins (whether neat, in the feed or in the drinking water) to the pregnant animal stimulates the intestine of the animal to produce antibodies to the pathogens, and this results in a marked decrease in the amount of pathogens excreted, with consequent improvement in the environment with benefit to both mother and her young. (With mammals antibodies produced in the colostrum and milk by the oral administration to the mother give further benefit to the suckling young.) Typical minimum dose rates are in the range 1 to 5 units (for measurement of a unit see in particular British Pat. No. 1,336,015) of endotoxins of each pathogenic strain of bacterium per animal per day. A particularly suitable level for inclusion in a feed is $10^2$ to $10^5$ units of the endotoxins of each pathogen per kilogram of feed.

In specifying as "endotoxins" the material to be introduced into the intestine, we do not mean to exclude from that material the presence of exotoxins or the presence of the cellular material within which the endotoxins are enclosed in the living bacterium; we mean merely that the endotoxins are of primary importance in obtaining the desired immunological effect while the exotoxins and cell debris are not. However it will on occasion be convenient to leave either exotoxins or cell debris or both associated with the endotoxins, first, to save the trouble of separating them; and secondly, to enable such antigenic capacity as they possess to be utilised. To act effectively the endotoxins are preferably freely available e.g. water-soluble. The endotoxins should of course as is described in British Pat. No. 1,336,015, be substantially free from the living pathogenic organism.

If the pregnant animal is a sow, notable enteropathogens against which protection is often desired are one or more of the E. coli serotypes which contain the endotoxins 08, 045, 0138, 0139, 0141, 0147, 0149 or 0157, or Clostridium welchii or Vibrio coli. If the pregnant animal is a cow, notable enteropathogens are E. coli serotypes which contain the endotoxins 08, 09, 015, 026, 078, 086, 0114, 0115, 0137 or 0139, or Salmonella dublin or typhimurium. If the pregnant animal is a ewe, notable enteropathogens are any of those already recited, or an E.coli serotype which contains the endotoxin 020. (With pregnant cows or ewes, the antigenic material can if desired be protected from possible degradation in the rumen and yet still be available for absorption in the small intestine: see Phillipson, Proc. Nutr. Soc. (1972) 31 159.)

When both injection and oral administration are employed, it is strongly preferred that the same endotoxin should be injected as is orally administered.

It is particular feature of the preferred form of the invention that only one injection is necessary. This is in sharp contrast to previous recommendations for parenteral injection of dams to give passive immunity to their young. A further important feature is that the injected material need not contain an adjuvant, such as an emulsion. Such adjuvants have been recommended previously to ensure gradual release of the injected material. This is unnecessary, indeed disadvantageous, in the present invention.

The named effective endotoxins of the enteropathogens are stable to heating at 100° C., and are conveniently obtained by a bacterium-sterilisation procedure which depends on heating, as described in our British Pat. No. 1,336,015. The preparation of feeds incorporating the endotoxins is also described there. A further technique is described in Example 4. Pathogens other than those described above can be significant, in particular for other species, and here of course the appropriate endotoxins have to be isolated and used.

As explained above repeated oral administration of endotoxins to the pregnant animal stimulates the intestine of the animal to produce antibodies to the enteropathogens, and this results in a marked decrease in the aount of enteropathogens excreted, with consequent improvement in the environment and benefit to both mother and her young. Additionally, the oral administration primes the blood circulatory, antibody system, so that antibody response to a parenteral injection of the endotoxins is much enhanced. As already stated, parenteral administration of the endotoxins is carried out towards the end of the gestation period, and this ensures high antibody activity during the period of colostrum formation, which is roughly the last 10 days of gestation.

Preferably, parenteral administration of the endotoxins is carried out 15–30 days before the estimated date of parturition, following a course of oral administration in which, daily or at least on alternate days, the endotoxins have been orally administered for the preceding 3 weeks, preferably the preceding 4 or 5 weeks, at a dose rate of 10–1000HI units (haemagglutination inhibition units) of the endotoxins of each serotype per animal per day. It is preferable to prolong oral administration until parturition, and even beyond, in order to minimise excretion of enteropathogens.

A convenient scheme is as follows (where S represents date of service by the sire):

|  | Pigs | Cattle | Sheep |
| --- | --- | --- | --- |
| Begin repeated oral administration in period | S to (S + 30) | S to (S + 190) | S to (S + 70) |
| Carry out parenteral administration in period | (S + 85) to (S + 270) | (S + 233) to (S + 130) | (S + 115) to |
| (S + 100) |  |  |  |
| Date of parturition | (S + 110) to (S + 115) | (S + 280) to (S + 290) | (S + 145) to (s + 150) |

The colostrum antibody titres resulting from such a regime are unexpectedly high. The passive immune status of the offspring is accordingly much enhanced, and their susceptibility to infection correspondingly reduced.

With the combined parenteral and oral immunisation of the special aspect of the invention, there is the special advantage that, in particular, the class of antibody IgM is produced in the colostrum, at least in that of the sow, in unexpectedly high proportion, whereas a normal parenteral immunisation schedule produces predominantly the much less effective antibody class IgG.

The invention is further illustrated by the following Examples, in which the endotoxins employed were those of E. coli and had been obtained following the procedure described in Example 3A of our British Pat. No. 1 336 015.

EXAMPLE 1

This Example illustrates the increase in concentration of antibodies in the serum and in the colostrum of in-pig sows that is attainable by the administration of antigenic bacterial matter both orally and parenterally.

Two matched groups of 8 sows were taken and those in group A were fed on a pig feed that was of standard kind except for the inclusion in it of the endotoxins of each of seven pathogenic strains of the bacterium E. coli, the strains having the O-antigen (endotoxins) serotype 08, 045, 0138, 0139, 0141, 0147 and 0149. Inclusion was at the level of 100 HI units (haemagglutination inhibition units; these are conveniently measured by the procedure set out in The Veterinary Record (1973) 92 630–636 or in Example 2c in our British Patent 1 336 015) per Kilogram of feed. The sows of Group B were fed on the standard feed *not* containing endotoxins.

Each group of sows was given its particular feed daily, from day S + 30 (where S represents the date of service by the boar) to at least day S + 115.

At day S + 94 each sow in each group was given a parenteral injection of 3000 HI units of the endotoxins (O-antigen) of each of the above-specified pathogenic E. coli serotypes.

At days S + 100 and S + 107, and at day F + 1 (where F represents date of farrowing) the serum of each sow was assayed for its content of antibodies. Immediately after parturition, the colostrum was also sampled and assayed for antibody content, so, too, was milk sampled and assayed on days F + 1, F + 2 etc. Results are set out in the table below.

| SOWS | | | | |
|---|---|---|---|---|
| | Concentration of antibodies in PHA units | | | |
| Date | Serum | | Colostrum or Milk | |
| | Group A | Group B | Group A | Group B |
| S + 100 | 640 | 80 | | |
| S + 107 | 1280 | 160 | | |
| F | 1280 | 160 | 2560 | 160 |
| F + 1 | 1250 | 80 | 640 | 80 |
| F + 2 | 1280 | 80 | 640 | 80 |
| F + 7 | 640 | 40 | 320 | 40 |
| F + 14 | 160 | 40 | 160 | 40 |

EXAMPLE 2

This Example compares the concentrations of antibodies in the serum of piglets born to treated and untreated sows.

The piglets born to the sows of the groups A and B of Example 1 were suckled normally by their dams, and their blood was assayed for antibody concentration. Results were:

| | PIGLETS | |
|---|---|---|
| | Concentration of antibodies in PHA units in serum | |
| Date | Group A | Group B |
| F | 0 | 0 |
| F + 1 | 2560 | 80 |
| F + 2 | 2560 | 80 |
| F + 7 | 320 | 40 |
| F + 14 | 80 | 10 |

There is a clear increase in the antibody titre of the piglets suckled by sows treated according to the invention.

By the wellknown method of gel filtration, colostrum from both groups of sows and serum from the piglets suckled by them were examined to determine the class of antibody present. It was found that for Group A sows the ratio of immunoglobulin IgM to immunoglobulin IgG was 10:1, whereas for Group B sows it was only 3:7. IgM is a far more potent antibacterial agent — by some 500 times — than IgG. Furthermore, IgM enhances the the subsequent development of *active* immunity in the developing young, whereas IgG tends to suppress that development.

EXAMPLE 3

This Example illustrates the improved ability of piglets suckled by Group A sows to overcome bacterial challenge.

24 hours after birth, both groups of piglets (i.e. piglets from Group A ad Group B sows) were challenged with an intravenous injection (1 ml) containing $5 \times 10^9$ live E. coli bacteria of serotype 0149:K91 K88a, c (L). Blood samples were taken during 1 hour immediately after injection, first at 5-minute intervals and then at 10-minute intervals, and the samples were assayed for the number of bacteria still living. Results were (in terms of organisms/ml of Blood):

| Time | Piglets of Group A sows | Piglets of Group B sows |
|---|---|---|
| 0 | $10^8$ | $10^8$ |
| 5 | $10^5$ | $10^8$ |
| 10 | $5 \times 10^4$ | $5 \times 10^7$ |
| 15 | $10^4$ | $2 \times 10^7$ |
| 20 | $10^3$ | $10^7$ |
| 25 | $<10^{3*}$ | $10^7$ |
| 30 | $<10^3$ | $5 \times 10^5$ |
| 40 | $<10^3$ | $10^5$ |
| 50 | $<10^3$ | $10^6$ |
| 60 | $<10^3$ | $10^7$ |

*$<10^3$ not assayable

In Group A, out of a group of 12 piglets there were no deaths and only three cases of mild hypothermia. In Group B (12 piglets), there was mild hypothermia in 4 pigs, and sever hypothermia and cyanosis in six. Of those six, four were dead within 3 hours of challenge.

EXAMPLE 4

Preparation of Endotoxin Material

The procedure of Example 8A was repeated except that after each final culture was produced it was heated to 60° C for 30 minutes to release the endotoxins and then cooled. 0.5 mls of formalin (40% formaldehyde) per 100 mls of culture was then added to each of the cooled cultures. The cultures containing the free endotoxins were then combined. The combined cultures were not given a further heat treatment.

EXAMPLE 5

Groups of sows matched to those used in Example 1 were handled as follows.

The sows of Group C were handled exactly like those of Group A except that they were not injected.

The sows of Group D were handled exactly like those of Group B except that they were not injected.

At farrowing the concentrations of antibodies in PHA units in the colostrum were

| Group A | Group B | Group C | Group D |
|---|---|---|---|
| 2560 | 160 | 80 | 20–40 |

Addendum: It is affirmed that the features described at page 8 lines 7 to 16 are all preferred rather than necessary features.

EXAMPLE 6

Preparation and isolation of endotoxins

Endotoxins are prepared from each of the seven E.-coli serotypes earlier referred to, following generally the method of Westphal, Lauderitz and Bister (1952) Z.Natur.Forsch. 7, 148.

A freeze-dried culture of E.coli is reconstituted in peptene water and incubated at 37° C. for 6 hours. After suitable growth the culture is checked for purity on a washed sheep blood agar plate, and then used to inoculate slopes of Nutrient Agar (Oxoid) in Roux flasks. The culture is grown at 37° C. overnight and the bacteria are harvested in sterile distilled water. The bacterial suspension obtained is dispensed aseptically into 30 ml Universal bottles and centrifuged at 4,000 rpm for 10 minutes. The supernatant liquid is removed, and the residual pellet of bacteria is resuspended in 4 ml of sterile distilled water and then freeze-dried.

In order to isolate endotoxins, 0.5 g of freeze-dried E.coli is suspended in 5 ml of 0.15M NaCl, and 10 ml of 90% aqueous phenol is added as lysing agent. The mixture is heated at 68° C. for 30 minutes with continuous agitation, following which it is centrifuged at 4,000 rpm to compact the cell debris. The aqueous phase is removed and cooled to 4° C., and to it are slowly added 10 volumes of ice-cold ethanol. The precipitate thus formed is redissolved in water, and nucleic acids are precipitated from the solution by addition of 2 volumes of ethanol, and removed. From the residual solution, endotoxins are precipitated by addition of a further 8 volumes of ethanol. They are separated by centrifugation, washed with ice-cold ethanol and re-dissolved in 0.15M NaCl. (This solution of endotoxins is referred to as Reagent 1.)

EXAMPLE 7

Assay of endotoxins a. Preparation of antiserum

Specific hyperimmune sera ('antisera') are prepared in New Zealand White rabbits against washed heat-killed (100° C, 2½ hours) organisms of each of the E.coli serotypes.

Suspensions of the heat killed organism are prepared in 0.15M NaCl (approx 3 × $10^9$ organisms/ml) and injected intravenously. The immunisation schedule begins with an injection volume of 0.1 ml and is continued on every fourth day with doubling volumes to 1.6 ml. The rabbits are bled 10 days following completion of the schedule, and the blood obtained is centrifuged. The upper layer of hyperimmune serum is collected. (This antiserum is referred to as Reagent 2.)

b. Measurement of antibody (anti-endotoxins) activity in antiserum

Sheep erythrocytes are sensitised by treating a 5% suspension of washed packed cells with an equal volume of the endotoxin solution Reagent 1 at 37° C. for 30 minutes. The sensitised cells are separated by centrifugation, washed free from excess endotoxins, and re-suspended in 0.15M NaCl to form a 2.5% suspension of endotoxin — sensitised sheep erythrocytes. (This is referred to as Reagent 3.)

Reagent 2 (the antiserum) is serially diluted with 0.15M NaCl to obtain a series of solutions of equal volume (1 vol) of antibody concentration 1/5, 1/10, 1/20, 1/40 ... $1/(5 \times 2^{n-1})$ that of Reagent 2, and to each of these solutions is added 1/5 vol of Reagent 3. Haemagglutination occurs in the stronger antiserum solutions and not in the weaker ones, and the end-point of the titration (assessed at 4° C.) is taken as that solution in which haemagglutination only just occurs. In a typical procedure, the end point might be at the twelfth solution i.e. at the solution having an antibody concentration $1/(5 \times 2^{11})$ that of Reagent 2. Reagent 2 would be said to have an antiserum titre of $5 \times 2^{11} (= 10,240)$.

c. Measurement of endotoxins concentration in solution of unknown concentration

The solution (Y) to be assayed is serially diluted with 0.15M NaCl to obtain a series of solutions of equal volume (3 vols) of endotoxins concentration 1/3, 1/6, 1/12, 1/24 & c that of the solution Y. To each of these solutions is added 1 vol of Reagent 2 (antiserum) diluted so as to have a titre of 20 (see b. earlier), and then (after a few minutes) 1 vol of Reagent 3 (sensitised sheep crythocytes) giving final endotoxin concentrations 1/5, 1/10, 1/20 ... $1/(5 \times 2^{n-1})$ that of solution Y. Haemagglutination is inhibited in the stronger endotoxin solutions but does occur in the weaker ones, and the end point of the titration is taken as that solution in which haemagglutination in only just inhibited. In a typical procedure this might be at the sixth solution, of endotoxins concentration $1/(5 \times 2^5)$ that of solution Y. Solution Y would then be said to have a titre of $5 \times 2^5 (=160)$, equivalent to 160 units of endotoxin per ml (see Example 8.)

EXAMPLE 8

A. Preparation of Endotoxin Material

The following procedure was separately followed for each of the E.coli serotypes earlier referred to.

(i) The bacterium was streaked out from a depository stock culture onto washed blood agar plates and incubated at 37° C. for 24 hours. The plates were then conventionally checked for purity of strain.

(ii) Colonies of the bacterium were transferred from the plates to 50 ml of Oxoid Nutrient Broth No. 2 (Catalogue No. CM 67). The broth was held at 37° C for 24 hours.

(iii) The whole culture obtained in (ii) was used to inoculate 1½ liters of Oxoid Nutrient Broth No. 2, and the broth was incubated, with shaking, at 37° C for 24 hours.

Each final culture thus produced contained about $10^{10}$ viable bacteria/ml, and a sample of the culture, when steamed at 125° C. for 2 hours and submitted to the assay procedure of Example 2, gave a titre of 2500, corresponding to 2560 units of endotoxin per ml of steamed culture. The cultures of all the serotypes were pooled and the pool was steamed for 2 hours in an autoclave (125° C.) to kill the bacteria.

B. Preparation of Pig Feed

The whole sterilised broth obtained from A is adjusted to pH 5 and incorporated in the weight ratio 15:85 in a conventional pig-weaning feed of the composition:

|  | % by weight |
|---|---|
| roller-dried skimmed milk | 20 |
| white-fish meal | 25 |
| rolled oat groats (oat flakes) | 36 |
| sugar (sucrose) | 10 |
| dried (yeast) (75% unextracted) | 5.5 |
| cod liver oil | 2 |
| sodium chloride | 0.5 |
| mineral supplement | 1.0 |

The resulting mash is dried at 65° C to a moisture level of about 15%.

EXAMPLE 9

The final culture of each serotype obtained following the procedure of A in Example 3 is centrifuged to separate the bacteria, which are then resuspended in water and heated at 125° C. for 30 minutes. The killed bacteria are then treated for 3 hours at 37° C. with a mixture of the enzymes lysozyme and pepsin, and the total endotoxins material resulting from the killing treatment and the enzymes treatment is assayed. The assayed endotoxins materials from all the serotypes are pooled, adjusted to pH 5, and added to skimmed milk. The mixture is then incorporated in a conventional pig feed of composition tabulated in Example 3, so as to give a concentration of $10^4$ units of the endotoxins of each serotype per kg of feed.

That is claimed is:

1. A method of treating a pregnant mammal whose young acquire, via the colostrum and gastro-intestinal wall, at least part of their passive immunity to gastro-intestinal disorders caused by infection with pathogenic bacteria, in which method effective amounts of endotoxins of one or more pathogenic bacteria strains, substantially free from the living pathogenic organisms, are administered both orally and parenterally to the mammal, said oral administration being carried out repeatedly during the gestation period, and said parenteral administration being carried out at least once towards the end of the gestation period to ensure high antibody activity during the period of colostrum formation.

2. A method according to claim 1 wherein parenteral administration is carried out at least once 15–30 days before the estimated date of parturition.

3. A method according to claim 2 wherein said parenteral administration is carried out following a course of oral administration in which, daily or at least on alternate days, said endotoxins have been orally administered at least for the preceding 3 weeks.

4. A method according to claim 3 wherein at least 1 HI unit of endotoxins of each pathogenic strain of bacterium is administered orally to said mammal each day.

5. A method according to claim 4 wherein oral administration is by use of a feed containing $10^2$ to $10^5$ HI units of endotoxins of each pathogenic strain per kilogram of feed.

6. A method according to claim 1 wherein said mammal is a sow and wherein the enteropathogens against which protection is obtained are one or more of the *E. coli* serotypes which contain the endotoxins 08, 045, 0138, 0139, 0141, 0149 or 0157, or *Clostridium welchii* or *Vibrio coli*.

7. A method according to claim 1 wherein said mammal is a cow and the enteropathogens against which protection is obtained are one or more of the *E. coli* serotypes which contain the endotoxins 08, 09, 015, 026, 078, 086, 0114, 0115, 0137 or 0139, or *Salmonella dublin* or *Salmonella typhimurium*.

8. A method according to claim 1 wherein said mammal is a ewe and the enteropathogens against which protection is obtained are one or more of the enteropathogens listed in claim 6 or in claim 7 or an *E. coli* serotype containing the endotoxins 020.

* * * * *